(12) United States Patent
Maad

(10) Patent No.: US 8,939,920 B2
(45) Date of Patent: Jan. 27, 2015

(54) PATIENT MONITORING AT RADIATION MACHINES

(75) Inventor: Kristofer Maad, Knivsta (SE)

(73) Assignee: C-Rad Positioning AB, Uppsala (SE)

( * ) Notice: Subject to any disclaimer, the term of this patent is extended or adjusted under 35 U.S.C. 154(b) by 722 days.

(21) Appl. No.: 12/665,644

(22) PCT Filed: Jun. 25, 2008

(86) PCT No.: PCT/SE2008/050778
§ 371 (c)(1),
(2), (4) Date: Dec. 18, 2009

(87) PCT Pub. No.: WO2009/011643
PCT Pub. Date: Jan. 22, 2009

(65) Prior Publication Data
US 2010/0198112 A1    Aug. 5, 2010

Related U.S. Application Data

(60) Provisional application No. 60/929,817, filed on Jul. 13, 2007.

(51) Int. Cl.
| | |
|---|---|
| *A61B 5/103* | (2006.01) |
| *A61B 19/00* | (2006.01) |
| *A61B 6/04* | (2006.01) |
| *A61B 6/00* | (2006.01) |
| *A61N 5/10* | (2006.01) |

(52) U.S. Cl.
CPC .......... *A61B 19/5225* (2013.01); *A61B 6/0457* (2013.01); *A61B 6/541* (2013.01); *A61N 5/1049* (2013.01); *A61B 19/5244* (2013.01); *A61B 2019/5265* (2013.01); *A61B 2019/5293* (2013.01); *A61B 2019/5437* (2013.01); *A61N 5/1064* (2013.01); *A61N 2005/1059* (2013.01)
USPC ....................................... 600/595; 250/492.1

(58) Field of Classification Search
USPC ........................................ 600/595; 250/492.1
See application file for complete search history.

(56) References Cited

U.S. PATENT DOCUMENTS

| | | | | |
|---|---|---|---|---|
| 5,622,187 | A  * | 4/1997 | Carol | 128/897 |
| 6,405,072 | B1 * | 6/2002 | Cosman | 600/426 |
| 2005/0143645 | A1 | 6/2005 | Vilsmeier | |

FOREIGN PATENT DOCUMENTS

WO    WO-2005/032647 A2    4/2005

OTHER PUBLICATIONS

Backman et al., "Registration of Anatomic Landmarks During Respiration Using Ultraviolet and Structured Lighting", Biomedical Visualization, Nov. 1995, pp. 42-49.
Maurer et al., "Registration of 3-D Images Using Weighted Geometrical Features", IEEE Transactions on Medical Imaging, vol. 15, No. 6, Dec. 1996, pp. 836-849.

* cited by examiner

*Primary Examiner* — Max Hindenburg
*Assistant Examiner* — Renee Danega
(74) *Attorney, Agent, or Firm* — Birch, Stewart, Kolasch & Birch, LLP

(57) ABSTRACT

The invention involves monitoring patient movement, in particular respiratory movement, of a patient (30) positioned on a couch (20) in connection with a radiation gantry (10). A 2D or 3D pattern (115) is projected onto the patient (30). At least a first portion of the pattern (115) is detected by a first detector (120) arranged on a first side of the gantry (10). At least a second portion of the pattern (115) is detected by a second detector (130) arranged on a second opposite side of the gantry (10). Pattern detection data is generated by the two detectors (120, 130) and is used for generating information representative of movement of the patient (30) on the couch (20). The information can be used, for instance, for prospective and/or retrospective gating.

29 Claims, 7 Drawing Sheets

PATIENT MONITORING AT RADIATION MACHINES

This application is the National Phase of PCT/SE2008/050778 filed on Jun. 25, 2008, which claims priority under 35 U.S.C. 119(e) to U.S. Provisional Application No. 60/929,817 filed on Jul. 13, 2007. All of which are hereby expressly incorporated by reference into the present application.

TECHNICAL FIELD

The present invention generally relates to patient monitoring in connection with radiation machines, and in particular to detection or monitoring of patient movement in connection with such radiation machines.

BACKGROUND

During the past decades there have been considerable developments within the fields of radiation therapy and medical diagnosis. The performance of external beam radiation therapy accelerators, brachytherapy and other specialized radiation therapy equipment has improved rapidly. Developments taking place in the quality and adaptability of radiation beams have included new targets and filters, improved accelerators, increased flexibility in beam-shaping through new applicators, collimator and scanning systems and beam compensation techniques, and improved dosimetric and geometric treatment verification methods have been introduced.

Furthermore, a number of powerful 3-dimensional diagnostic techniques have been developed, ranging from computed tomography (CT), positron and single photon emission computed tomography (PET and SPECT) to ultrasound and magnetic resonance imaging and spectroscopy (MRI and MRS). Equally important is the increased knowledge of the biological effect of fractionated uniform and non-uniform dose delivery to tumors and normal tissues and new assay techniques, including the determination of effective cell doubling times and individual tissue sensitivities, allowing optimization of the dose delivery to tumors of complex shape and advanced stages.

A major problem in the field of radiation therapy and diagnosis today is the movement of a patient on a patient couch during radiation therapy or diagnosis. The movement can be inevitable, such as the movement of the patient body caused by breathing, or the patient may slightly adjust his/her position or posture on the couch.

In volumetric imaging, including CT, PET, MRI, MRS or SPECT, the resulting images will contain artifacts, e.g. blurring and discontinuities, since the whole volume is not being acquired at a single respiratory phase/amplitude. These artifacts are due to, among others, the respiratory-induced movement of at least a portion of the patient body during image data acquisition.

In radio therapeutic treatment, the tumor and surrounding tissue will undergo displacement and deformation due to the respiration during the treatment delivery, and this will cause an uncertainty in the distribution of the dose delivered.

One solution to these problems is to monitor the patient's breathing and use this respiratory signal to "gate" the imaging or treatment, either prospectively or retrospectively. In prospective gating, the imaging or treatment process is controlled so that it will only be active during a specified respiratory gating window—when the phase or amplitude of the respiratory signal is within certain pre-defined limits. In retrospective gating, which is only applicable during imaging, the respiratory signal is captured in parallel with the volumetric imaging process and these are typically synchronized to a common time base. After the scan is completed, the respiratory signal is used as a key to sort the volumetric data parts acquired into different "buckets", where each bucket contains volumetric data acquired during a specified respiratory gating window. This allows combination of several complete volumetric images, each from a specific respiratory amplitude/phase.

There are today several techniques available at the market for acquiring the respiratory signal. For example, the Philips CT gating system uses a belt that is fastened around the patient's chest. This belt is employed for measuring the chest displacement due to respiration. Varian uses another technique for respiratory movement monitoring, see for example document [1]. This technique involves placing a block with retro-reflective markers on the patient's chest. The movement of the chest due to breathing can then be tracked by an infrared (IR) camera with an integrated IR light source.

SUMMARY

The solution taken by Philips CT gating system is marred by the usage of a cumbersome belt that has to be attached to the patients each and every time they are to be diagnosed by a CT system. The usage of a detectable block positioned on the patient chest has a major disadvantage in that the block may actually move slightly on the chest during CT imaging, thereby resulting in problems with respiratory movement processing.

The present invention overcomes these and other drawbacks of the prior art arrangements.

It is a general patient of the present invention to provide a patient monitoring that does not require the attachment of any objects to the patient body for the purpose of monitoring patient movement.

It is another patient of the invention to provide a patient monitoring that can be used in connection with different radiation gantry designs.

These and other patients are met by the invention as defined by the accompanying patent claims.

Briefly, the present invention involves monitoring patient movement, in particular respiratory-induced movement, of a patient positioned on a patient couch in connection with an imaging or therapeutic radiation gantry or machine. The patient monitoring arrangement of the invention comprises a pattern projector arranged connected to or in the vicinity of the gantry for providing a two or three dimensional pattern on the patient on the couch. A first pattern detector is arranged connected to or in the vicinity of the gantry and on a first side of the gantry. This first detector detects at least a first portion of the pattern on the patient and generates first detection data based on the detected at least a first pattern portion. A second pattern detector is arranged connected to or in the vicinity of the gantry but on a second opposite side of the gantry. The second detector detects at least a second portion of the pattern on the patient and generates second detection data based on the detected at least a second pattern portion. A pattern analyzer connected to the two detectors processes the first and second detection data to generate information representative of the movement of the patient on the couch. This information can be in the form of respiratory amplitude or respiratory data samples.

The generated information is reflective of the current patient body position at the particular measurement instance. By performing the pattern detection at multiple time instances during an imaging or therapeutic session, it is possible to in, or at least close to, real time follow the (respiratory-induced) movement of the patient. The information can therefore be used for diagnostic and/or therapeutic prospective gating and/or diagnostic retrospective gating.

In a preferred embodiment, the current patient and couch position is determined through the usage of a position marker attached to the patient couch. This marker can then be detected by at least one of the pattern detectors. The marker detection is employed for generating a signal representative of the current couch position, which signal is used together with the pattern detection data for generating the movement-representative information.

SHORT DESCRIPTION OF THE DRAWINGS

The invention together with further patients and advantages thereof, may best be understood by making reference to the following description taken together with the accompanying drawings, in which.

DETAILED DESCRIPTION

Figure 1:
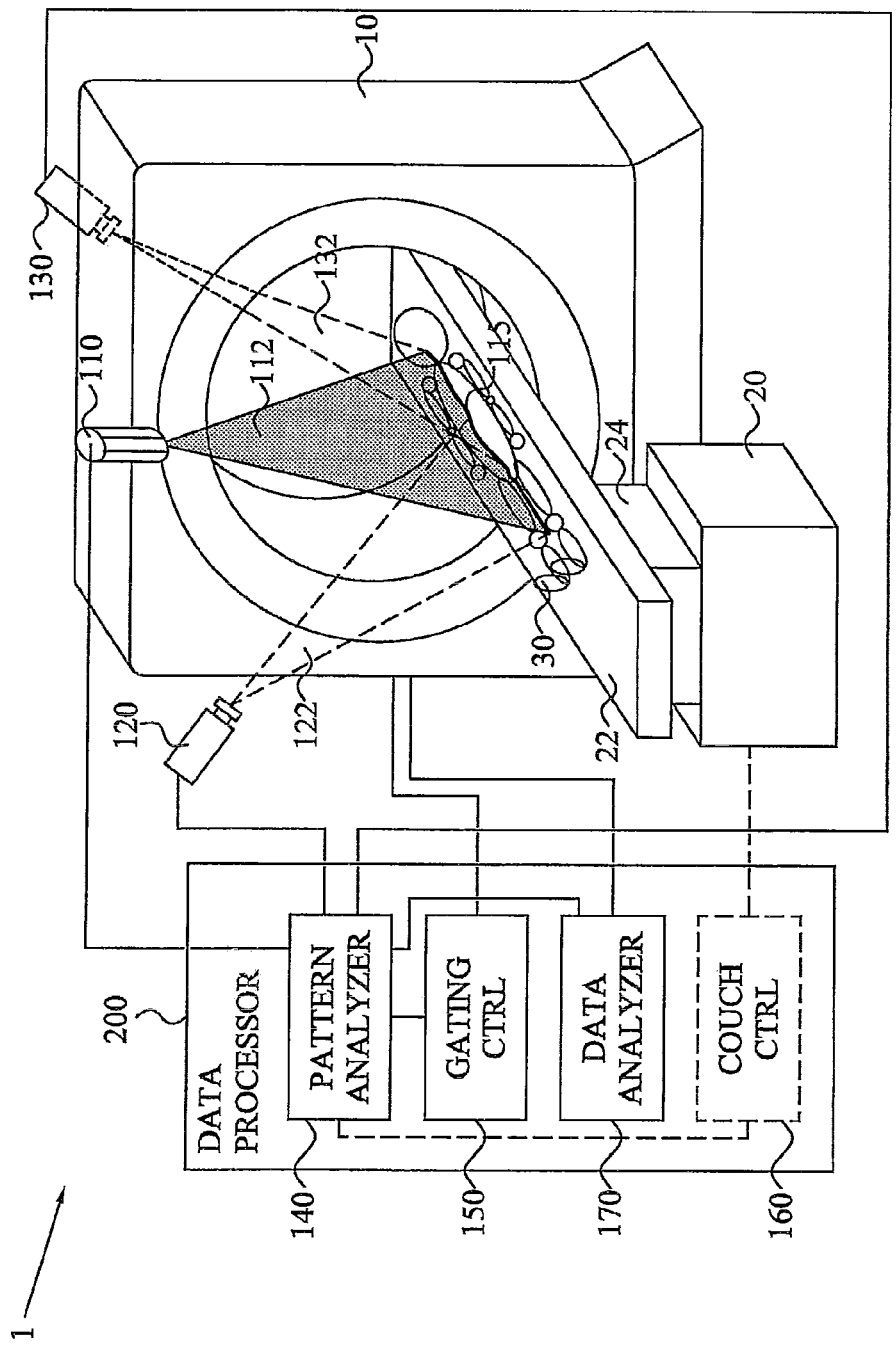
FIG. 1 is a schematic overview of a radiation gantry equipped with a patient monitoring arrangement according to an embodiment of the present invention.

Throughout the drawings, the same reference characters will be used for corresponding or similar elements.

The present invention relates to a non-contact method and arrangement of acquiring respiratory signal and other patient movement signals without the need of physically placing any markers or other items such as blocks or belts on or around the patient's body. The present invention is specifically designed to be used with imaging or radio therapeutic equipment or indeed any other equipment that can benefit from respiratory gating. The present invention can be applied to vastly different gating designs and can advantageously be used in connection with imaging or radio therapeutic systems having a ring-shaped gantry, where the treatment couch and the patient are moving through the gantry during the imaging or treatment process.

Briefly, the process involved in detecting and monitoring patient movement, such as respiratory-induced movement, and producing a movement or respiratory signal can generally be divided into three steps:

1) Surface measurement, which is performed in a non-contact way according to the present invention;
2) Determination of current patient couch position; and
3) Computation of the respiratory signal based on the surface measurements and the current couch position.

Surface Measurement

A particular suitable method of non-contact surface measurement according to the present invention is to project a two or three dimensional pattern onto the patient and then detect the pattern on the patient body. Such a method can preferably use a laser line or pattern triangulation for non-contact measurement of the patient surface. However, the present invention is not limited thereto but can use other non-contact methods of line or surface measurement, including, but not limited to, photogrammetry with or without active or passive structured light. Other such techniques include shape from shading, depth from focus/defocus and phase measurement profileometry.

The non-contact surface method should be able to measure at least a portion of the patient's body surface either as a point cloud/mesh or as a line, preferably in the sagittal plane, i.e. along the patient's centerline, or indeed any other two or three dimensional pattern.

A problem with such non-contact surface methods is that the radiation gantry will obstruct the view at least during a part of the patient and couch movement into the gantry, in particular for ring-shaped gantries. The present invention solves this problem by having at least two pattern detectors arranged on either sides of the radiation gantry. This means that the present invention is able to perform surface or line measurements from both sides of the gantry in parallel.

From the center of the gantry, the surface measurement setup preferably should cover a distance D in both directions along the rotational axis of the axis, to be able to, while the patient moves through the gantry, monitor the same location on the patient's chest or abdomen for as long as its respiratory motion at that location affects the patient's anatomy at the imaging or treatment plane of the gantry.

A coordinate system for the measured points is used. In this description, the IEC Fixed coordinate system is assumed, with the origin placed at the (rotational) center of the gantry, the positive z axis pointing up, the positive x axis pointing to the right and the positive y axis pointing towards the gantry when standing in front of it, looking at it. It is obviously possible to select any other coordinate system without changing the main ideas of the invention.

Laser Line Triangulation

This section will provide additional details for using the laser line triangulation method.

Any gantry-integrated sagittal laser positioning light can be used in this setup, or dedicated external sagittal room lasers can be used, possibly one on each side of the gantry. The mentioned laser(s) is (are) preferably active during the whole imaging or treatment session since the projected laser line is used for triangulation.

Two cameras, such as charge-coupled device (CCD) cameras, are fixed in the room, attached to or built-in the imaging or therapy machine housing. They are placed on each side of the gantry. In this context more than two cameras can be used. Thus, the present invention can be used in connection with M+N cameras or pattern detectors, where M of these detectors are arranged on a first side of the radiation gantry and N detectors are arranged on a second opposite side of the radiation gantry, wherein M, N are positive integers. The cameras are preferably mounted at an angle to the sagittal plane, where this angle $\alpha$ can be in the range of $0°<\alpha\leq90°$ and more preferably $1°\leq\alpha\leq90°$.

When using laser line triangulation, camera calibration is typically first performed in order to establish the relationship between the room coordinate system, such as IEC fixed coordinate system, and each camera's pixels. Such camera calibration is well-known in the art and is not described further herein.

The cameras should be placed and directed so that their combined field of view covers, regardless of the (variations of) surface height of the patient lying on the couch, a contiguous part of the laser line projected on the patient, extending the specified distance D in both directions from the center of the gantry. With such an approach it is possible to continuously keep a specific monitored location on the patient's chest or abdomen in view as the patient moves through the gantry.

During the imaging or treatment session, the triangulation will typically be done separately for each camera, producing measurements of the surface height (z) along part of the projected laser line (y) or projected pattern (x, y).

The two datasets can be merged into a single dataset, typically append one to the other and then sorting the points according to the displacement along the y axis or along the x and y axes.

For more information of laser triangulation and other non-contact surface geometry measurement techniques, reference is made to document [2], the teachings of which is hereby incorporated by reference.

Determination of the Current Couch Position

In order to continuously compute the surface height at a specific location on the patient's chest or abdomen while the patient moves through the gantry, it is necessary to know where the couch is.

A possible solution is to integrate with the couch control logic to continuously monitor the couch position. This is the preferred method if the couch coordinates are readily available in this manner. However, it has the disadvantage that integration may not be that easily performed and requiring dedicated implementation for different models of imaging and treatment equipment.

An alternative is to install a marker on the side of couch that is visible from a camera (or two cameras). If cameras are used for surface measurement, such as in the case of line triangulation described above, a light emitting diode (LED) could be used as couch marker. In such case, the LED can have the same wavelength as the laser line or projected pattern so that it will be visible through any bandpass filter mounted on the cameras. This LED should be arranged on the patient couch so that it is detectable, i.e. in view, for the whole range of couch motion.

Using the camera three dimensional calibration data, together with the fact that the couch is generally only possible to move in two degrees of freedom in these kinds of equipment with ring-shaped gantries, it is possible to continuously calculate the couch position.

Computation of the Respiratory Signal

The user operating the equipment typically performs two steps in order to enable the generation of the respiratory signal:
1) Move the patient couch so that the location of the patient to be monitored, typically in the chest or abdomen region, is in the imaging or treatment plane of the radiation gantry; and
2) Mark this location in the gating system, for instance by pushing a hardware button, performing an action of a graphical user interface, activating a soft key, etc. When marking the location, the current couch coordinates are recorded by the described gating system.

Once the patient's surface has been measured, at least along the centerline, and the current couch position is known, the current y coordinate in the room of the marked location on the patient is obtainable.

It is then a matter of interpolating a z value at the determined y location and the resulting z value will be the current amplitude of the respiratory signal.

The present invention will now be described in more detail in connection with particular implementation embodiments thereof.

FIG. 1 is a schematic overview of a radiation machine 1 with a radiation gantry 10 and equipped with a patient monitoring arrangement of the present invention. The radiation gantry 10, which could be a radiation-based imaging or therapeutic gantry, has an associated patient couch 20 adapted for receiving a patient 30 to be diagnosed or treated.

The patient couch 20 comprises a couch top 22 that is movable relative the couch base. The movement of the couch top 22 can be performed manually. Alternatively, the couch 20 can comprise equipment 24 for automatically moving the couch top in response to a movement control signal.

The patient monitoring arrangement of the present invention comprises at least one pattern projector 110 arranged in the room for providing a two or three dimensional (2D or 3D) pattern 115 onto the patient 30 when positioned on the patient couch. In the figure, this pattern 115 has non-limitedly been illustrated as a 2D pattern 115, i.e. a line projected along a substantial length of the patient body 30. The line 115 is preferably a laser line that is substantially parallel with an anteroposterior axis of the patient 30 and more preferably lies in the sagittal plane of the patient.

The pattern projector 110 is preferably arranged for vertically projecting the laser line 115 onto at least a portion of the patient 30. The line 115 is preferably projected onto at least the surface portion of the patient that lies above a tumor or treatment volume to be irradiated by the radiation gantry 10 or a body portion to be imaged by the radiation gantry 10. The projected line 115 preferably extends at least partly into an opening of the gantry 10 adapted for receiving the patient couch 20.

Instead of using a single pattern projector 110, the patient monitoring arrangement can use multiple pattern projectors 110, possibly arranged on either sides of the radiation gantry 10. In such a case, a first pattern projector can be arranged on a first side of the gantry 10 for providing a first 2D or 3D sub-pattern onto the patient 30. A second pattern projector is then arranged on a second opposite side of the gantry 10 for providing a second 2D or 3D sub-pattern onto the patient 30. These two 2D or 3D sub-patterns collectively form a 2D or 3D pattern that is detected by the patient monitoring arrangement.

The patient monitoring arrangement also comprises a first pattern detector 120 arranged on a first side of the radiation gantry 10 for detecting at least a first portion of the 2D or 3D pattern 115 on the patient 30. Based on this pattern detection, the pattern detector 120 generates first detection data that is input to a pattern analyzer 140 of a data processor 200. A corresponding second pattern detector 130 is arranged on a second opposite side of the gantry 10 for detecting at least a second portion of the 2D or 3D pattern 115 on the patient 30. This second detector 120 also generates second detection data based on the detected pattern. This second detection data is forwarded to the connected pattern analyzer 140.

The first side is the front side of the gantry 10 while the second side is the back side of the gantry 10 as illustrated in the figure.

The two detected portions of the pattern 115 at least partly overlap as illustrated in the figure. This overlap could be complete so that both detectors 120, 130 will, at least some time during the patient 30 and couch 20 movement into the gantry 10, detect the same pattern portion. However, in most cases the two detectors 120, 130 will, due to their mutual arrangements, fields of view and current couch position, detect different portions of the 2D or 3D pattern 115 on the patient 30, though these different portions at least partly overlap.

It is anticipated by the present invention that during a typical imaging or radio therapeutic session, only the first pattern detector 120 might be able to detect the 2D or 3D pattern 115 as the patient couch 20 is initially fully retracted and dose not extend into the gantry 10. However, during the session the couch top 22 and patient 30 are moved towards and into the gantry 10. This will enable also the second pattern detector 130 to detect at least a portion of the projected pattern 115 on the patient 30. At this point both detectors 120, 130 will generate pattern detection data. If the couch movement continues further it can actually be possible that the first detector 120 will no longer be able to see the projected pattern 115 as the gantry 10 will block the line of sight of the first detector 120. However, at this point, detection data can still be collected by the second pattern detector 130.

Thus, the patient monitoring arrangement of the present invention can utilize pattern detection data of the first pattern detector 120, detection data of the second pattern detector 130 and detection data collected (simultaneously or in parallel) by both the first 120 and second 130 detectors.

The pattern detection performed by the at least two pattern detectors 120, 130 of the invention are preferably performed at multiple different time instances during the imaging or therapeutic session. For example, pattern detection can be performed every k μs, every k ms or every k s, where k is a number larger than zero and is dictated by the sampling frequency of the detectors 120, 130. The detection is preferably performed through the whole session but could alternatively instead be conducted during selection time intervals of the session.

As was described in the foregoing, the pattern detectors 120, 130 are preferably arranged to detect the projected pattern 115 in projection planes 122, 132 having a non-zero angle relative a vertical plane 112 through the patient. Usage of such non-zero angles between detection planes 122, 132 and projection plane 112 facilitates usage of a triangulation method, such as laser line triangulation.

The patient monitoring arrangement preferably also comprises a pattern analyzer 140 connected to the first pattern detector 120 and the second pattern detector 130. This analyzer 140 uses the detection data from the detectors 120, 130 for generating information representative of movement of the patient 30. This data analysis can be performed as previously described. Thus, the analyzer 140 is able to produce information or data indicative of the respiratory level or amplitude. However, also other patient movements can be detected and quantized by the patient monitoring arrangement of the present invention.

The information can be used as gating information and is then provided to a gating controller 150. This controller 150 will control the diagnostic or therapeutic irradiation of the patient 30 by the radiation gantry 10, thereby enabling a prospective gating. Thus, the gating controller 150 controls the gantry so that the imaging or treatment process is only active during specified respiratory gating windows identified by the gating controller 150 based on the information provided by the pattern analyzer 140. Thus, the provided information can be amplitude of the respiratory signal at a selected patient portion and then the gating controller 150 can selectively activate or inactivate the radiation delivery from the gantry 10 or, in the case of a diagnostic session, alternatively selectively active or inactive the radiation detection at the gantry 10 based on the actual values of the respiratory signal amplitude.

Alternatively, or in addition, the information from the pattern analyzer 140 can be forwarded to a data analyzer 170 that is connected to a radiation detector (not illustrated) arranged in the gantry 10. This radiation detector is provided for collecting and generating diagnostic data. The information generated by the pattern analyzer 140 can then be provided to the data analyzer 170 for the purpose of enabling a retrospective gating. Thus, the diagnostic data is processed based on the information from the pattern analyzer 140 to sort the diagnostic data based on the time interval of the respiratory cycle the data was collected.

As was described in the foregoing, the patient monitoring arrangement preferably also collects data regarding the current couch position in addition to the pattern detection. In such a case, a couch controller 160 can be provided for generating a position signal representative of a current position of the couch top 22 movable by a couch motor 24. The position signal is forwarded from the couch controller to the pattern analyzer 140 and is used together with the pattern detection signals for generating the information representative of the patient movement.

The pattern analyzer 140 of the present invention can be implemented on a data processor 200, such as computer, provided in the treatment room or preferably in another location but is then connected to the pattern detectors 120, 130 and preferably the pattern projector 110. This data processor 200 or separate such processor(s) can also house the gating controller 150, the data analyzer 170 and the couch controller 160.

Figure 2:
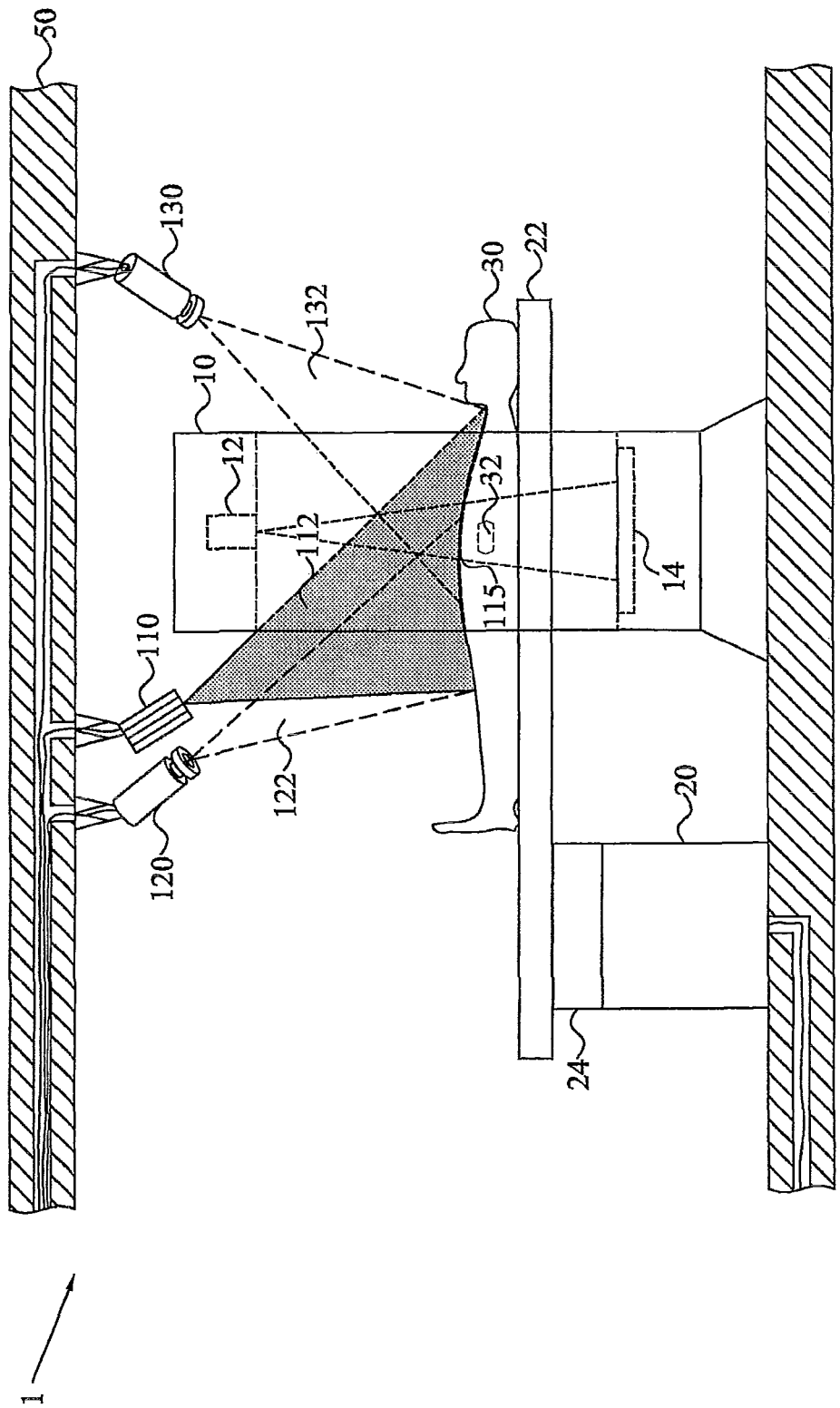
FIG. 2 is a side-view of a radiation gantry equipped with a patient monitoring arrangement according to an embodiment of the present invention.

FIG. 2 is a side-view of a radiation machine 1, such as a therapeutic or diagnostic radiation machine, equipped with a patient monitoring arrangement according to the present invention. In this illustrative embodiment, the pattern projector 110 and the pattern detectors 120, 130 are attached to the ceiling 50 of the radiation room. This figure clearly illustrates the mutual arrangement of the two detectors 120, 130 on either sides of the gantry 10 for allowing detection of the projected pattern 115 throughout the whole imaging or therapeutic session even though the patient 30 and couch top 22 is moved into the gantry 10.

The figure also illustrates a schematic radiation source 12 of the gantry 10 and a radiation detector 14 that can be used for detecting the radiation from the source 12 passing through at least a portion of the patient body 30. A schematic tumor 32 is also illustrated in the figure.

Figure 3:
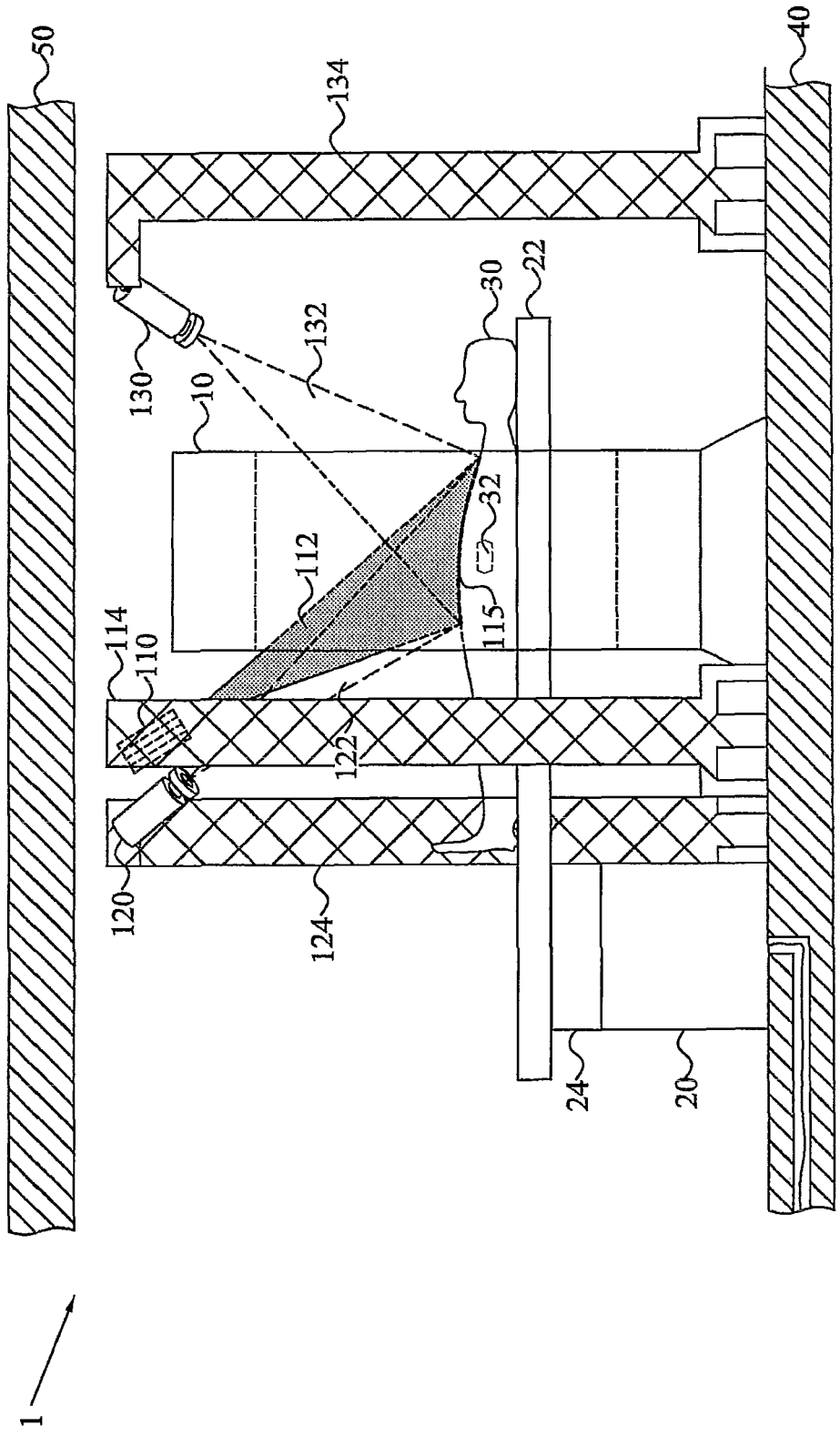
FIG. 3 is a side-view of a radiation gantry equipped with a patient monitoring arrangement according to another embodiment of the present invention.

FIG. 3 is another side-view of a radiation machine 1 equipped with a patient monitoring arrangement of the present invention. In this embodiment, the pattern projector 110 and the at least two pattern detectors 120, 130 are arranged on dedicated frames or scaffolds 114, 124, 134 attached to the floor 40 or walls of the radiation room. This means that the projector 110 and detectors 120, 130 can be moved between different radiation gantries 10 in different radiation rooms.

Figure 4:
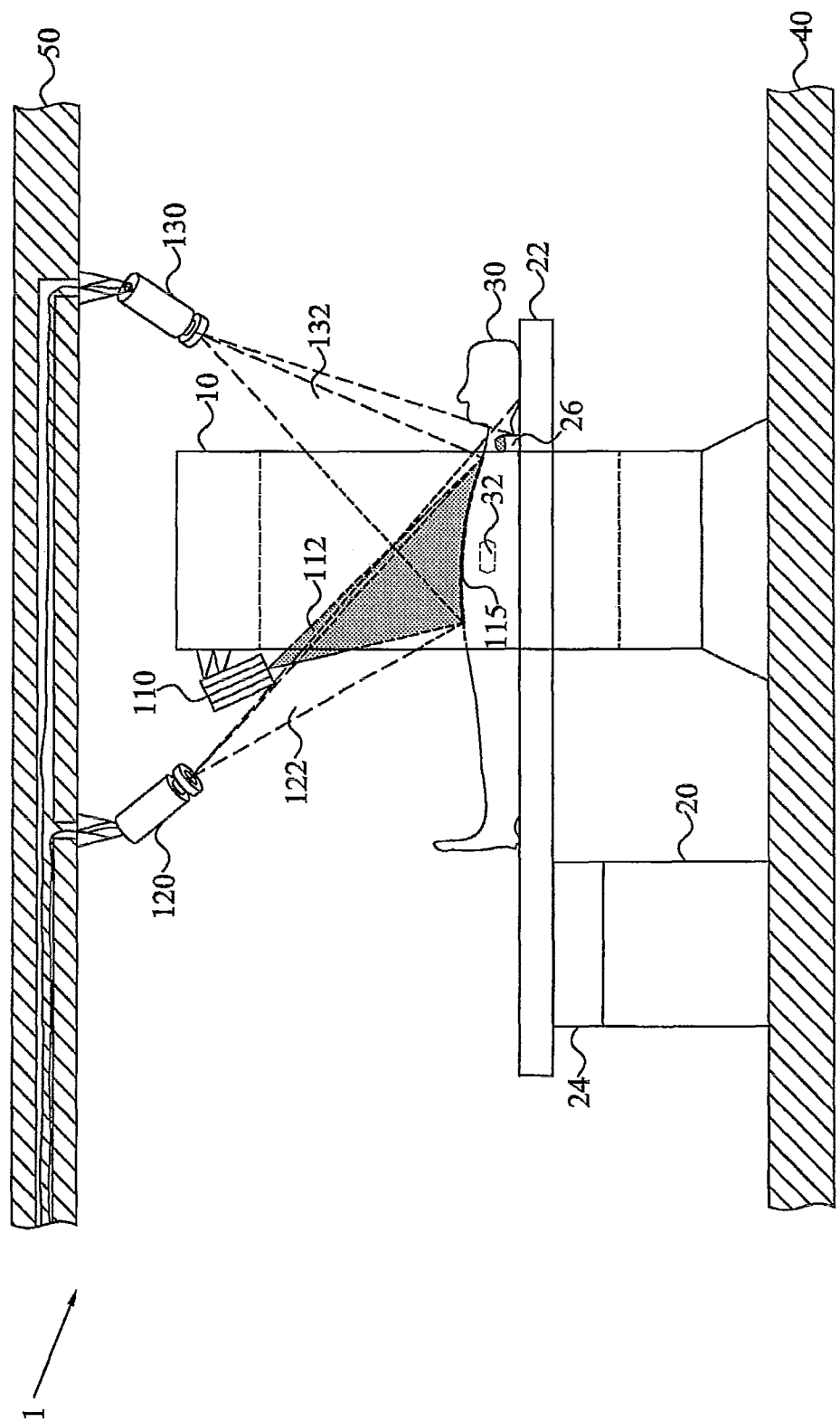
FIG. 4 is a side-view of a radiation gantry equipped with a patient monitoring arrangement according to a further embodiment of the present invention.

FIG. 4 is a further side-view of a radiation machine 1 equipped with a patient monitoring arrangement of the present invention. In this embodiment, the pattern projector 110 is attached to the housing of the radiation gantry 10, while the detectors 120, 130 are attached to the ceiling 50.

The teachings of the embodiments disclosed in FIGS. 2 to 4 can be combined. Thus, the pattern projector 110 and the detectors 120, 130 can, independently of each other, be arranged on the ceiling 50, on a frame attached to a wall or standing on the floor 40 or be attached to the radiation gantry 10. In these FIGS. 2 to 4, the pattern analyzer has not been illustrated but will in practice be connected to the detectors 120, 130 and preferably the projector 110.

FIG. 4 also illustrates the usage of a couch or position marker 26 that can be detected by a dedicated marker detector (not illustrated) or more preferably by at least one of the two pattern detectors 120, 130. In the latter case, the position marker 26 is preferably a LED having a same light wavelength as the wavelength of the pattern 115 projected by the pattern projector 110. The detection of this position marker 26 can then be used for determining the y coordinate(s) of the monitored portion of the projected pattern 115 as previously described.

Figure 5:
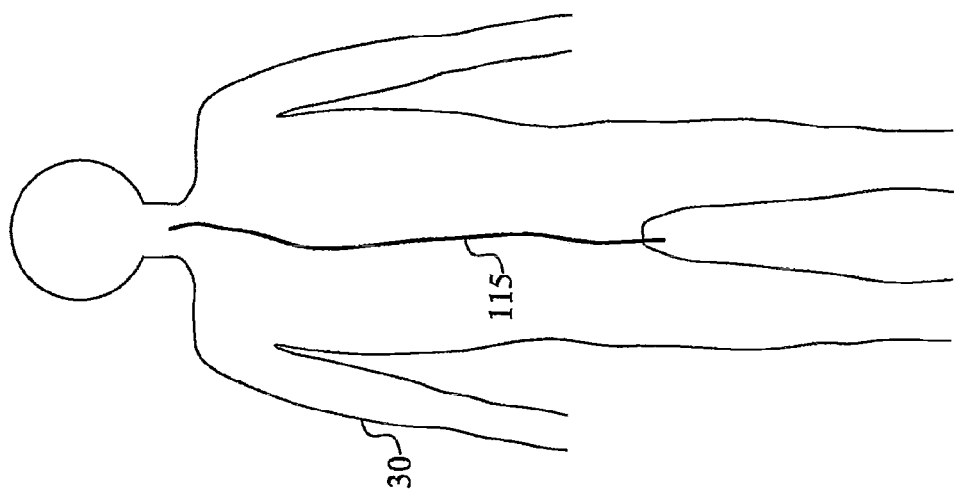
FIG. 5 is a schematic representation of a detectable two dimensional pattern projected onto a patient according to the present invention.

FIG. 5 illustrates a patient 30, onto which a 2D pattern in the form of a (laser) line 115 is projected according to the present invention. As is seen in the figure the line 115 is preferably substantially parallel with the anteroposterior axis of the patient and more preferably lies in the sagittal plane of the patient 30. The line 115 preferably extends over a substantial portion of the patient upper body, including the chest and abdominal. For respiratory gating purposes, the projected line 115 is preferably long enough to cover at least a portion of the chest of the patient 30 during the whole movement of the patient 30 and couch into gantry.

Figure 6:
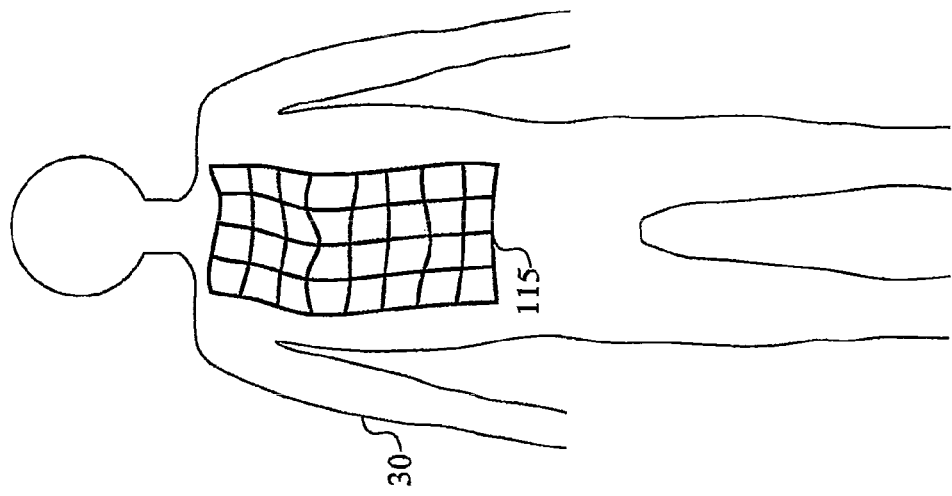
FIG. 6 is a schematic representation of a detectable three dimensional pattern projected onto a patient according to the present invention.

FIG. 6 illustrates a possible 3D pattern in the form of a grid or mesh 115 projected onto the patient 30. The projected 2D or 3D patterns of the present invention do not necessarily have to be contiguous patterns but could instead consist of multiple points and dots that together form a 2D or 3D pattern.

Usage of a 2D or 3D pattern projected on a patient, such as illustrated by the embodiments of FIGS. 5 and 6, provides several significant advantages to the present invention. As the pattern of the invention is an extended pattern along the patient body it is actually possible to detect and monitor several spatially separated body portions or points. Thus, the movement of both the abdominal body portion and the thorax can simultaneously be monitored and detected by the present invention. Such dual detection points, or having more than two such points on the body surface, significantly improves the accuracy or providing a secure and reliable gating. As a consequence, the pattern detectors of the present invention are preferably configured for each detecting multiple, i.e. at least, spatially separated points of the projected pattern on the body portion. In such a case, the invention can be used for simultaneously detecting and monitoring both abdominal and thoracal (respiratory) movements of the patient.

In such a case, the pattern analyzer of the invention generates information representative of the movement of at least a first portion of the patient and a second portion of the patient on the couch based on the detection data from the two detectors.

Another big advantage of the projected 2D/3D pattern of the present invention is that the selection of detection/monitoring points along the projected line (FIG. 5) or pattern (FIG. 6) can be made retrospectively. In such a case, the pattern detectors detect at least a portion of projected pattern corresponding to spatially separated portions on the body surface. In such a case, it is possible to, once detection data and diagnostic data have been collected according to the invention, determine which detection point(s) on the patient surface to use as a signal basis for the purpose of generating the patient movement descriptive information. For instance, in a first patient a first set of thoracal points best represents the internal movement of tissues and organs of interest, while for a second patient a set of abdominally situated points is more appropriate. This means that the invention allows identification and usage of the point or those points that "best" correlates to internal (tissue/organ) movement for every patient and at every particular radiation occasion.

In such a case, the pattern analyzer generates information representative of the movement of multiple spatially separated points or portions of the patient body based on the detection data from the detectors. The data analyzer processes this information and preferably further input from a user deciding which of the multiple body points to use as movement reference.

This should be compared to prior art techniques discussed in the background section, where one is limited to a single fixed detection point corresponding to the particular belt position. With such a technique it is not possible to retrospectively change detection point.

Figure 7:
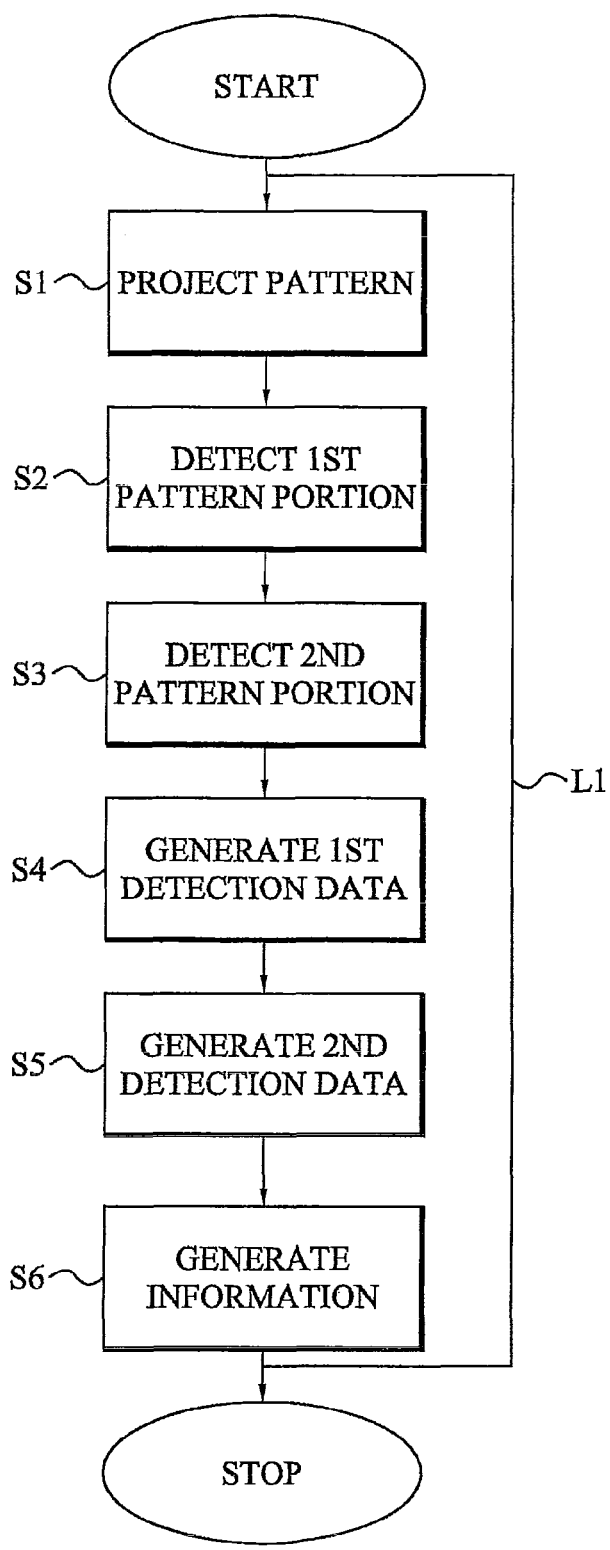
FIG. 7 is a flow diagram of a patient monitoring method according to the present invention.

FIG. 7 is a flow diagram of a patient monitoring method according to the present invention. The method starts in step S1, where a 2D or 3D pattern is projected onto a patient positioned on a patient couch of a radiation gantry. A next step S2 detects, on a first side of the gantry, at least a first portion of the projected pattern on the patient. A corresponding step S3 detects, on a second opposite portion of the gantry, at least a second portion of the pattern projected on the patient. Step S4 generates first detection data based on the detected at least a first pattern portion and step S5 generates second detection data based on the detected at least a second pattern portion. Information representative of movement of the patient on the couch is generated in step S6 based on the first and second detection data. The pattern projection, pattern detection and data and information generation of the method is preferably performed at multiple time instances during an imaging or therapeutic session, which is schematically illustrated by the line L1.

Figure 8:
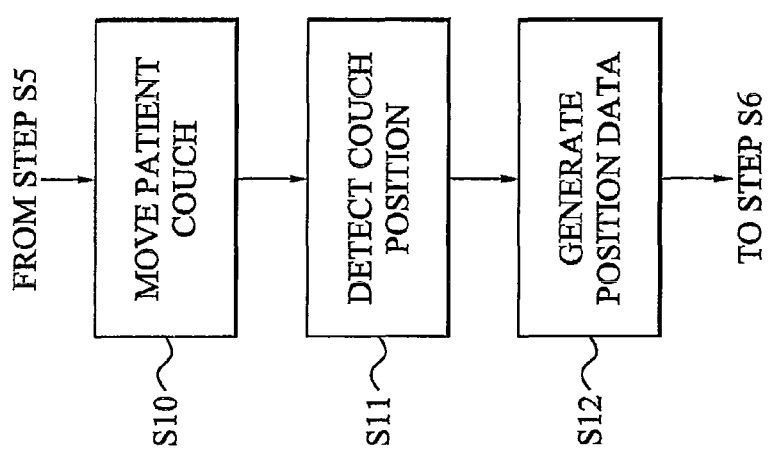
FIG. 8 is a flow diagram illustrating additional steps of the patient monitoring method of FIG. 7.

FIG. 8 is a flow diagram illustrating additional steps of the patient monitoring method of the present invention. The method continues from step S5 of FIG. 7. A next step S10 moves the patient couch and therefore the patient towards and into the radiation gantry. Step S11 detects a current position of the patient, typically based on a current position of the patient couch. This detection can be performed based on a control unit adapted for transmitting couch movement control signals to a couch moving unit. Alternatively, the couch is equipped with a position marker that can be detected, typically by at least one of the pattern detectors. In either case, position data is generated in step S12 based on the detected current position. This position data is used together with the detected pattern data in step S6 of FIG. 7 for generating the information representative of the movement of the patient, typically respiratory movement, on the couch.

Figure 10:
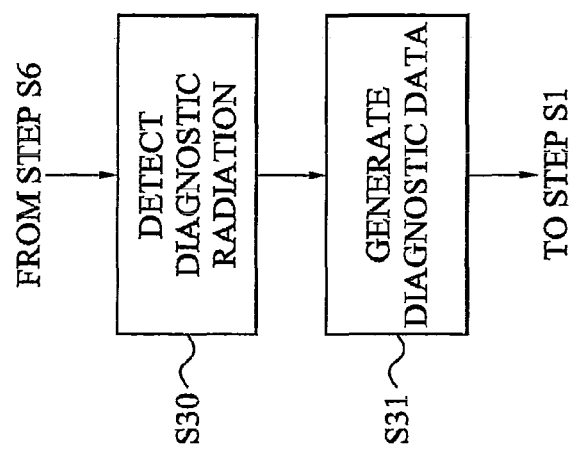
FIG. 10 is a flow diagram illustrating additional steps of the patient monitoring method of FIG. 7.
Figure 9:
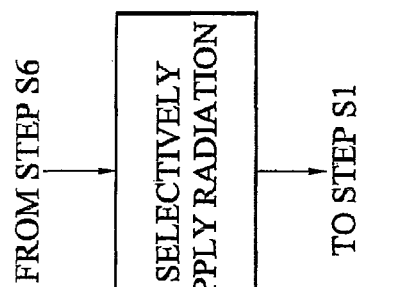
FIG. 9 is a flow diagram illustrating an additional step of the patient monitoring method of FIG. 7.

FIG. 9 is a flow diagram illustrating an additional step used for providing a prospective gating. The method continues from step S6 of FIG. 7. In a next step S20, radiation is selectively applied by the radiation gantry based on the movement representing information generated in step S6 of FIG. 7. FIG. 10 correspondingly illustrates additional steps used for providing a retrospective gating. The method continues from step S6 of FIG. 7. A next step S30 detects diagnostic radiation using a radiation detector of the gantry. This detected radiation is used together with the movement representing information from step S6 of FIG. 7 for generating diagnostic patient data by processing the detected diagnostic data in response to current respiratory signal amplitude.

The teachings of the present invention is not limited to the particular ring-shaped gantry designs shown in the figures but can be applied to other gantry designs and radiation machines.

It will be understood by a person skilled in the art that various modifications and changes may be made to the present invention without departure from the scope thereof, which is defined by the appended claims.

REFERENCES

[1] U.S. Pat. No. 7,177,386
Gareth Bradshaw, "Non-Contact Surface Geometry Measurement Techniques", Image Synthesis Group, Trinity College, Dublin, Ireland, 1999

The invention claimed is:

1. A patient monitoring arrangement adapted for use in connection with a radiation system comprising a radiation gantry including a tubular opening and an associated patient couch, said patient monitoring arrangement comprises:
a pattern projector configured to project a two or three dimensional pattern onto at least a portion of a patient positioned on said patient couch, said pattern extending at least partly into said tubular opening of said radiation gantry adapted for receiving said patient couch;
a first pattern detector arranged on a front side of said radiation gantry including said tubular opening, for detecting at least a first portion of said pattern on said patient and generating first detection data based on said detected at least a first portion;
a second pattern detector arranged on an opposite back side of said radiation gantry including said tubular opening, for detecting at least a second portion of said pattern on said patient and generating second detection data based on said detected at least a second portion; and
a pattern analyzer connected to said first pattern detector and said second pattern detector for generating information representative of movement of said patient on said patient couch based on first detection data and said second detection data.

2. The arrangement according to claim 1, wherein said second portion of said pattern at least partly overlaps said first portion of said pattern.

3. The arrangement according to claim 1, wherein said pattern analyzer is arranged for generating information representative of movement of multiple spatially separated points on a surface of said patient on said couch based on the detection data from the two detectors.

4. The arrangement according to claim 3, further comprising a data analyzer for processing said information and selecting a reference point of said multiple spatially separated points.

5. The arrangement according to claim 1, wherein said pattern projector is arranged for providing a laser line onto a body surface said patient, said first pattern detector is arranged for detecting at least a first portion of said laser line and said second pattern detector is arranged for detecting at least a second portion of said dimensional laser line.

6. The arrangement according to claim 1, wherein said pattern includes a line and said pattern projector is arranged for projecting said line onto at least an abdominal portion and a chest portion of said patient.

7. The arrangement according to claim 1, wherein said pattern includes a line and said pattern projector is arranged for projecting said line onto said at least a portion of said patient and in a sagittal plane of said patient.

8. The arrangement according to claim 1, wherein said pattern includes a line and said pattern projector is arranged for vertically projecting said line onto said at least a portion of said patient.

9. The arrangement according to claim 8, wherein said pattern includes a line and said first pattern detector is arranged for detecting said line in a first projection plane having a first non-zero angle relative a vertical plane through said patient and said second pattern detector is arranged for detecting said line in a second projection plane having a second non-zero angle relative said vertical plane.

10. The arrangement according to claim 9, wherein said pattern analyzer is arranged for generating said information based on line triangulation using said first detection data and said second detection data.

11. The arrangement according to claim 1, wherein said patient couch comprises a movable couch top and a couch position marker connected to said movable couch top, at least one of said first and second pattern detectors being arranged for detecting a current position of said position marker and generating position data based on said detected current position, said pattern analyzer is arranged for generating said information based on first detection data, said second detection data and said position data.

12. The arrangement according to claim 1, wherein said patient couch comprises a movable couch top and a position determining unit arranged for generating position data representative of a current position of said movable couch top, said pattern analyzer is connected to said position determining unit and is arranged for generating said information based on first detection data, said second detection data and said position data.

13. A radiation machine comprising:
a patient monitoring arrangement as defined in claim 1;
a patient couch; and
a radiation gantry for selectively irradiating a patient positioned on said patient couch based on information representative of movement of said patient on said patient couch generated by said patient monitoring arrangement.

14. A diagnostic radiation machine comprising:
a patient monitoring arrangement as defined in claim 1;
a patient couch;
a radiation gantry providing diagnostic radiation to a patient positioned on said patient couch;
a radiation detector for detecting said diagnostic radiation; and
a diagnostic data analyzer for generating diagnostic patient data based on said detected diagnostic radiation and information representative of movement of said patient on said patient couch generated by said patient monitoring arrangement.

15. The arrangement according to claim 1, wherein
said first pattern detector is arranged connected to the gantry and on a first side of the gantry, and
said second pattern detector is arranged connected to the gantry and on a second, opposite side of the gantry.

16. The arrangement according to claim 1, wherein
said first pattern detector is arranged on a first side of the gantry and spaced from the gantry, and
said second pattern detector is arranged on a second, opposite side of the gantry and spaced from the gantry.

17. The arrangement according to claim 1, wherein said first pattern detector is arranged on a front side of said tubular opening, and said second pattern detector is arranged on an opposite back side of said tubular opening.

18. The arrangement according to claim 1, wherein at least one of
said first pattern detector arranged on the front side of said radiation gantry, and
said second pattern detector arranged on the opposite back side of said radiation gantry is not connected to the radiation gantry.

19. The arrangement according to claim 1, wherein said pattern is a line projected onto at least a portion of the patient positioned on said patient couch, said line being substantially parallel with an anteroposterior axis of said patient and extending at least partly into said tubular opening of said radiation gantry adapted for receiving said patient couch.

20. A patient monitoring arrangement adapted for use in connection with a radiation system comprising a radiation gantry and an associated patient couch, said patient monitoring arrangement comprises:
a pattern projector configured to project a two or three dimensional pattern onto at least a portion of a patient positioned on said patient couch, said pattern extending at least partly into an opening of said radiation gantry adapted for receiving said patient couch;
a first pattern detector arranged on a front side of said radiation gantry for detecting at least a first portion of said pattern on said patient and generating first detection data based on said detected at least a first portion;
a second pattern detector arranged on an opposite back side of said radiation gantry for detecting at least a second portion of said pattern on said patient and generating second detection data based on said detected at least a second portion,
wherein
a detected part of said at least a first portion of said pattern detected by said first pattern detector is not in the field of view of said second pattern detector, or
a detected part of said at least a second portion of said pattern detected by said second pattern detector is not in the field of view of said first pattern detector; and
a pattern analyzer connected to said first pattern detector and said second pattern detector configured to generate information representative of movement of said patient on said patient couch based on said first detection data and said second detection data generated based on said at least a first portion of said pattern and said at least a second portion of said pattern, and to obtain information representative of the patient movement detected from the front side of the radiation gantry and from the back side of the radiation gantry.

21. A patient monitoring method comprising:
projecting a line onto at least a portion of a patient positioned on a patient couch associated with a radiation gantry, said line being substantially parallel with an anteroposterior axis of said patient and extending at least partly into an opening of said radiation gantry adapted for receiving said patient couch;
detecting, on a front side of said radiation gantry, at least a first portion of said line on said patient;
generating first detection data based on said detected at least a first portion;
detecting, on an opposite back side of said radiation gantry, at least a second portion of said line on said patient;
generating second detection data based on said detected at least a second portion; and
generating information representative of movement of said patient on said patient couch based on first detection data and said second detection data.

22. The method according to claim 21, wherein
projecting said line comprises projecting a laser line onto said patient,
detecting on said front side comprises detecting at least a first portion of said laser line, and
detecting on said opposite back side comprises detecting at least a second portion of said laser line.

23. The method according to claim 21, wherein projecting said line comprises projecting said line onto at least an abdominal portion and a chest portion of said patient.

24. The method according to claim 21, wherein projecting said line comprises projecting said line onto said at least a portion of said patient and in a sagittal plane of said patient.

25. The method according to claim 21, wherein
projecting said line comprises vertically projecting said line onto said at least a portion of said patient,
detecting on said front side comprises detecting said line in a first projection plane having a first non-zero angle relative a vertical plane through said patient, and
detecting on said opposite back side comprises detecting said line in a second projection plane having a second non-zero angle relative said vertical plane.

26. The method according to claim 21, further comprising:
moving a couch top of said patient couch, said couch top comprising a couch position marker;
detecting a current position of said position marker; and
generating position data based on said detected current position, wherein generating said information comprises generating said information based on first detection data, said second detection data and said position data.

27. A radiation provision method comprising:
generating information representative of movement of a patient on a patient couch as defined in claim 21; and
selectively irradiating said patient positioned on said patient couch based on said information.

28. A method of processing diagnostic patient data comprising:
generating information representative of movement of a patient on a patient couch as defined in claim 21;
detecting radiation applied by a radiation gantry onto said patient on said patient couch; and
generating diagnostic data by collectively processing said information and said detected diagnostic radiation.

29. The method according to claim 28, wherein generating said information comprises:
projecting a line onto said patient positioned on said patient couch, said line being substantially parallel with an anteroposterior axis of said patient and extending at least partly into an opening of said radiation gantry adapted for receiving said patient couch;
detecting, on a front side of said radiation gantry, at least a first portion of said two or three dimensional pattern on said patient; and
detecting, on an opposite back side of said radiation gantry, at least a second portion of said two or three dimensional pattern on said patient, at least one of detecting on said front side and detecting on said opposite back side is performed simultaneously as said radiation gantry applies said radiation onto said patient.

* * * * *